(12) United States Patent
Ciulla et al.

(10) Patent No.: US 10,231,718 B2
(45) Date of Patent: Mar. 19, 2019

(54) TISSUE EXTRACTION DEVICES AND RELATED METHODS

(71) Applicant: Boston Scientific Scimed, Inc., Maple Grove, MA (US)

(72) Inventors: Ronald Ciulla, Westford, MA (US); Kenneth P. Reever, Hopedale, MA (US); Jozef Slanda, Milford, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 453 days.

(21) Appl. No.: 14/719,623

(22) Filed: May 22, 2015

(65) Prior Publication Data

US 2015/0335393 A1    Nov. 26, 2015

Related U.S. Application Data

(60) Provisional application No. 62/002,292, filed on May 23, 2014.

(51) Int. Cl.

| | |
|---|---|
| *A61B 17/122* | (2006.01) |
| *A61B 17/00* | (2006.01) |
| *A61B 90/00* | (2016.01) |
| *A61B 18/24* | (2006.01) |
| *A61B 18/00* | (2006.01) |
| *A61B 17/06* | (2006.01) |
| *A61B 17/12* | (2006.01) |
| *A61B 17/128* | (2006.01) |
| *A61B 17/29* | (2006.01) |

(52) U.S. Cl.
CPC ........ *A61B 17/00234* (2013.01); *A61B 90/39* (2016.02); *A61B 17/06166* (2013.01); *A61B 17/122* (2013.01); *A61B 17/12013* (2013.01); *A61B 17/1285* (2013.01); *A61B 18/24* (2013.01); *A61B 2017/00274* (2013.01); *A61B 2017/2924* (2013.01); *A61B 2018/00547* (2013.01); *A61B 2018/00982* (2013.01); *A61B 2090/3908* (2016.02); *A61B 2090/3912* (2016.02); *A61B 2090/3937* (2016.02); *A61B 2090/3991* (2016.02); *A61B 2217/005* (2013.01)

(58) Field of Classification Search
CPC ............ A61B 17/00234; A61B 17/122; A61B 17/1227; Y10T 24/20–24/206
USPC .................... 606/151, 157, 158, 221; 24/511
See application file for complete search history.

(56) References Cited

U.S. PATENT DOCUMENTS

| | | | | |
|---|---|---|---|---|
| 4,696,081 A | * | 9/1987 | Yen ......................... | B42F 1/006 24/558 |
| 4,735,438 A | * | 4/1988 | Demarest, Jr. ........... | B42D 9/00 24/67.3 |
| 5,304,183 A | * | 4/1994 | Gourlay ........... | A61B 17/00234 227/901 |

(Continued)

*Primary Examiner* — Kathleen Holwerda
(74) *Attorney, Agent, or Firm* — Bookoff McAndrews, PLLC

(57) ABSTRACT

A marking device may include a body. The body may be configured to transition between a closed configuration and an open configuration. The body may further include two arms. A distal end of each arm may be coupled to a distal end of the body. The marking device may further include a suture coupled to the body. Application of a force on a proximal end of each arm may be configured to cause the body to transition between the closed configuration and the open configuration.

16 Claims, 8 Drawing Sheets

(56) References Cited

U.S. PATENT DOCUMENTS

| | | | | |
|---|---|---|---|---|
| 5,569,274 A | * | 10/1996 | Rapacki | A61B 17/00234 |
| | | | | 128/898 |
| 5,571,121 A | * | 11/1996 | Heifetz | A61B 17/122 |
| | | | | 606/151 |
| 6,716,226 B2 | * | 4/2004 | Sixto, Jr. | A61B 17/122 |
| | | | | 606/142 |
| 2007/0032807 A1 | * | 2/2007 | Ortiz | A61B 17/12 |
| | | | | 606/153 |
| 2011/0082347 A1 | * | 4/2011 | Okoniewski | A61B 17/0218 |
| | | | | 600/227 |

* cited by examiner

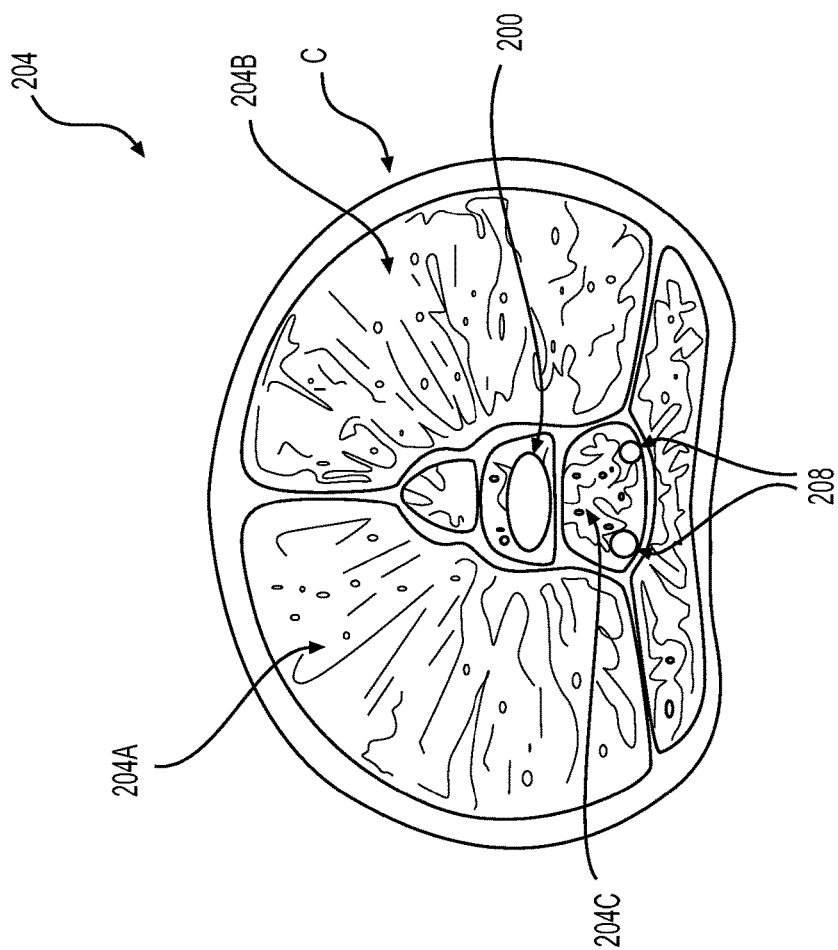

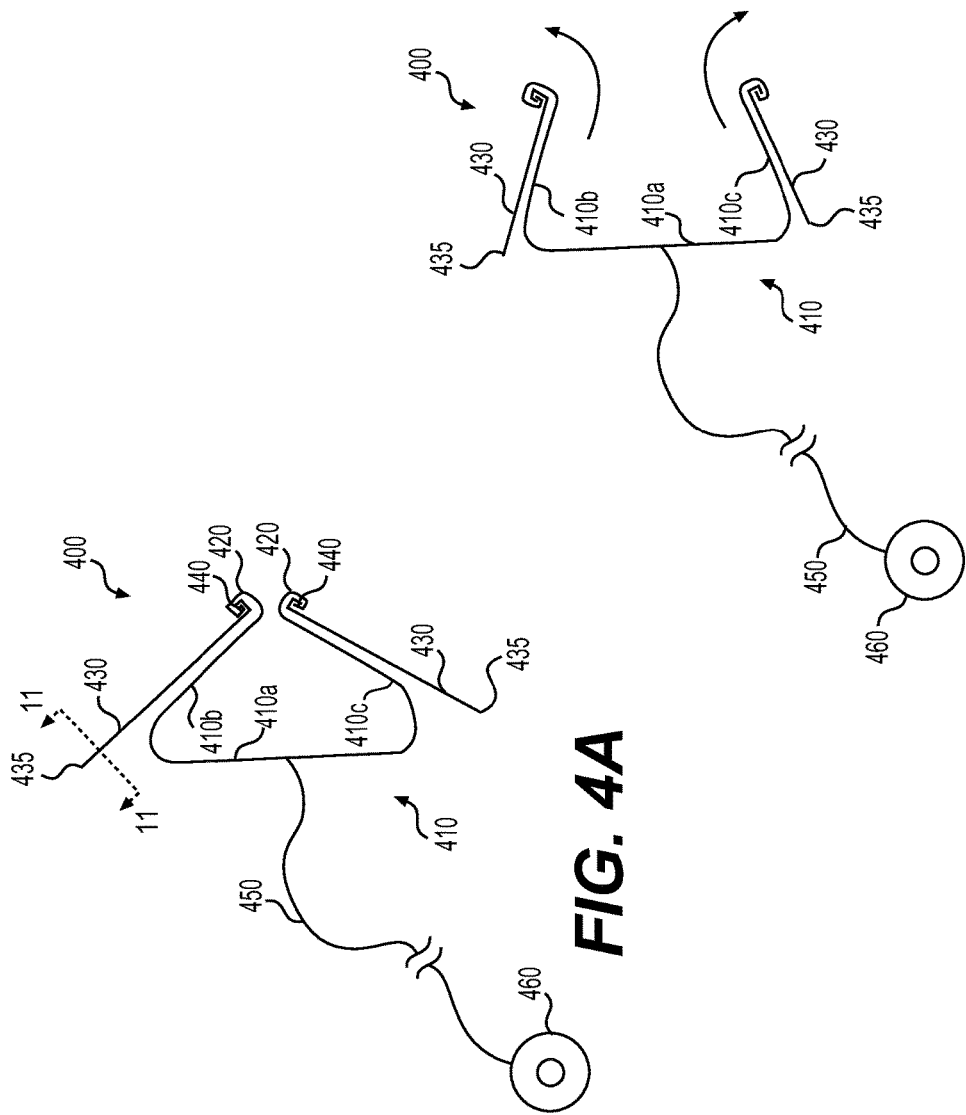

TISSUE EXTRACTION DEVICES AND RELATED METHODS

CROSS REFERENCE TO RELATED APPLICATIONS

This application claims the benefit of U.S. Provisional Application No. 62/002,292, filed May 23, 2014, the disclosure of which is incorporated herein by reference in its entirety.

DESCRIPTION OF THE DISCLOSURE

Field of the Disclosure

Examples of the present disclosure relate generally to medical devices and procedures. In particular, examples of the present disclosure relate to medical devices and methods for tissue enucleation and extraction.

Background of the Disclosure

Benign Prostatic Hyperplasia (BPH) is noncancerous enlargement of the prostate gland in men. BPH includes hyperplasia (an increase in the number of cells) of prostatic stromal and epithelial cells which result in the formation of large nodules in the periurethral region of the prostate. As the prostate enlarges it puts pressure on and/or partially or completely occludes the urethra. Additionally, prostate enlargement may cause pain, difficulty in urination, infection, or the like.

Enucleation of the Prostate (EP) is a technique for treating BPH. EP typically involves inserting an energy emitting device into the urethra and directing the device to target tissue including enlarged prostate tissue. Typically, such energy emitting devices are directed to target tissue using a sheath such as, for example, a laserscope, a cystoscope, a nephroscope and/or rectoscope. The energy emitting device enucleates (e.g., separates or removes) the target prostate tissue away from its surroundings. Typically the separated prostate tissue may form one or more large pieces of tissue, referred to as "tissue balls", which are then directed (e.g., pushed) into the bladder using the energy emitting device or another medical device. While referred to herein as a "ball," the severed tissue may not necessarily be in the shape of a ball (e.g., sphere) but rather, may have any shape including irregular shapes. The energy emitting device is then removed and another device such as a morcellator or other extraction tool is introduced into the sheath for removing the tissue. A morcellator is a surgical device having a small opening at its distal end, one or more cutting blades, and suction capability. The blades may cut (e.g., mince, puree) the large pieces of tissue, e.g., tissue balls, that were moved into the bladder into smaller pieces. These smaller pieces may then be removed from the body through the opening via, suction and/or other means.

EP procedures often require great skill and typically are performed by very experienced medical professionals. The procedure is "blind," in that incisions are made within the prostate without a readily ascertainable sense of the "depth" or geometry of the prostate. As such, extreme care must be used so as to not inadvertently harm (e.g., cut, damage, etc.) unintended portions of the prostate gland, including, for example, the prostatic capsule which lines the prostate gland. Such challenges result in a long learning curve for medical professionals before they become efficient with the EP technique. Accordingly, it may be desirable to provide for improved systems and methods for tissue enucleation and extraction.

SUMMARY OF THE DISCLOSURE

Examples of the present disclosure include medical devices, such as a marker, that may be used to indicate selective target tissue portions to be separated from remaining tissue portions, and methods of use thereof.

In one example, a marking device may be disclosed. The marking device may include a body. The body may be configured to transition between a closed configuration and an open configuration. The body may further include two arms. A distal end of each arm may be coupled to a distal end of the body. The marking device may further include a suture coupled to the body. Application of a force on a proximal end of each arm may be configured to cause the body to transition between the closed configuration and the open configuration.

The marking device may further include one or more of the following features: the body may comprise a clip; in the open configuration, the body may define a receiving space; the receiving space may be configured to retain tissue therein; the body may further include two legs; a distal end of each leg may include a rounded lip; distal end of each arm may be received within the rounded lip of a respective leg; a shape of each distal end of each arm may be complementary to a shape of each lip; in the open configuration, distal ends of each leg may be spaced from one another by a first distance, and wherein in the closed configuration, the distal ends of each leg may be spaced from one another by a second distance, wherein the first distance may be greater than the second distance; the body may comprise at least one of stainless steel, plastic, and Nitinol; the suture may include a length sufficient to extend externally of a patient when the marking device is internal of a patient; a handle member may be coupled to a proximal end of the suture; the body, in the closed configuration, may be triangular shaped; the body may be a single-use device; and an insertion device may be configured to pass the body therethrough.

In an additional or alternative example, a marking system for treating BPH may be disclosed. The marking system may include an adjustable ligation member configured to transition between a first collapsed configuration and a second expanded configuration. The marking system may further include a suture coupled to the adjustable ligation member and a manipulation tool. The manipulation tool may include a working element on a distal end thereof. The working element may be configured to grasp tissue. The adjustable ligation member may be sized so as to be placed about grasped tissue in the second expanded configuration, and tightened about the grasped tissue in the first collapsed configuration.

The marking system may further include one or more of the following features: the working element may include a pair of forceps positioned on a distal end of the manipulation tool; and the tissue may include prostate tissue.

In an additional or alternative example, a method of treating tissue is disclosed. The method may include delivering a marking device to a position proximate target tissue. Additionally, the method may include adjusting the marking device to transition between a closed configuration and an open configuration and securing the marking device on the target tissue while in the open configuration. The method may further include severing the target tissue from remaining tissue portions while the marking device is secured on the target tissue.

The method may further include one or more of the following features: wherein severing the target tissue may include enucleating the target tissue so as to be separated from remaining tissue portions; urging the severed target tissue and marking device into a bladder of a patient; morcellating the target tissue within the bladder; and coupling a morcellator device to the marking device via a suture.

Additional objects and advantages of the present disclosure will be set forth in part in the description which follows, and in part will be understood from the description, or may be learned by practice of the claimed disclosure. The objects and advantages of the claimed disclosure will be realized and attained by means of the elements and combinations particularly pointed out in the appended claims.

It is to be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate exemplary features of the present disclosure and together with the description, serve to explain the principles of the disclosure.

FIG. 3 illustrates a cross-sectional top-view of a prostate suffering from BPH;

FIG. 4A illustrates an exemplary marking device in a closed configuration according to a first example;

FIG. 4B illustrates the marking device of FIG. 4A in an open configuration;

DETAILED DESCRIPTION

Reference will now be made in detail to features of the present disclosure, examples of which are illustrated in the accompanying drawings. Wherever possible, the same reference numbers will be used throughout the drawings to refer to the same or like parts. As used herein, the term "distal" refers to the direction that is away from the user and into the patient's body. By contrast, the term "proximal" refers to the direction that is closer to the user and away from the patient's body.

Overview

Examples of the present disclosure may include a medical device for removing and/or retrieving a material from a body and methods of use thereof. In some embodiments, the medical device may be used to retrieve tissue that has been cut away or otherwise severed from its surroundings. In at least one embodiment, the tissue to be removed may be tissue from the prostate for treatment of BPH. In alternative embodiments, the medical device may be used to remove other types of tissues or materials such as, for example, bladder stones, kidney stones, and the like. For convenience, the exemplary medical devices discussed herein are referred to as marking devices; however, these references are merely made for convenience, and are intended to include devices capable of other and/or additional operations and/or functions.

In the following sections, embodiments of the present disclosure will be described using the prostate as an exemplary body organ. It will be understood that the prostate is merely an example and that the disclosed devices may be utilized in other parts of the body.

The present disclosure provides medical devices for marking, enucleating, and removing tissue from a patient's body. The medical devices may be used to remove tissue that has been cut away or excised from the body. The disclosed devices may be configured to be introduced into the body through a suitable natural opening, such as through the urethra.

Exemplary Embodiments

Figure 1:
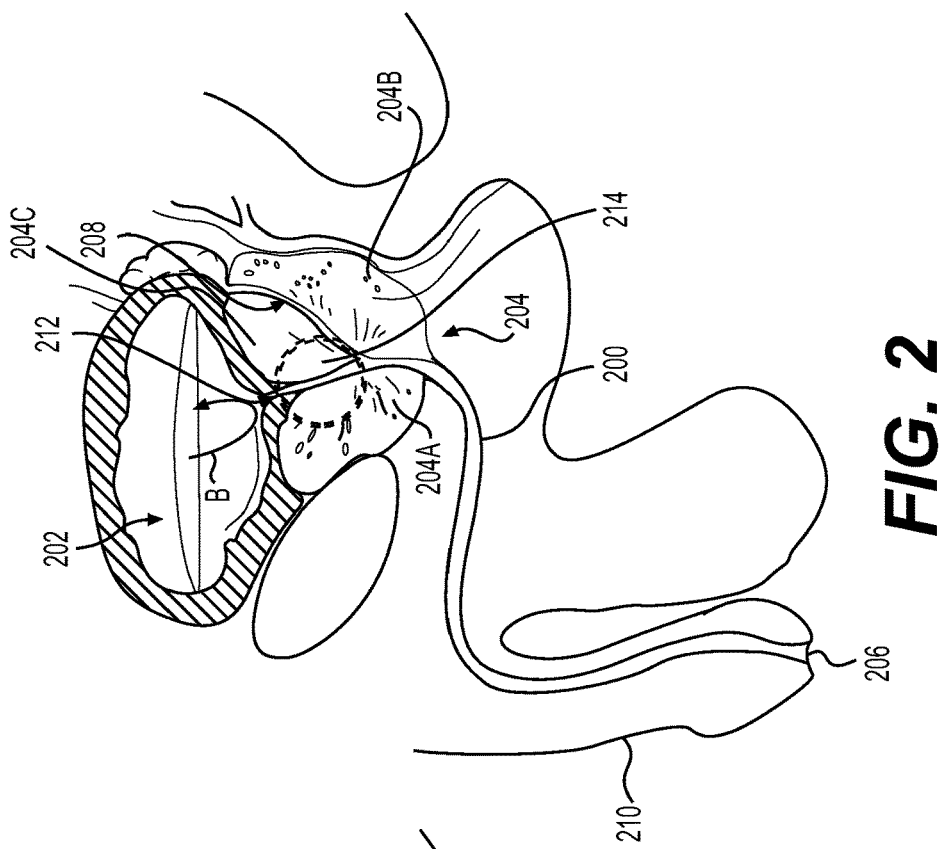
FIG. 1 illustrates a male pelvic region with a healthy urinary system.

FIG. 1 illustrates the pelvic region of a male having a healthy urinary system. As shown in FIG. 1, the urinary system includes a urethra 100, a bladder 102, a prostate 104, a urinary meatus 106, and an ejaculatory duct 108 of the male urinary system. The urethra 100 is a biological lumen connecting bladder 102 to the urinary meatus 106 at the tip of the penis 110. The urethra 100 connects to the bladder 102 at bladder opening 112. As shown, the prostate 104 is positioned around the urethra 100 between the bladder 102 and the penis 110. The prostate 104 is comprised of multiple lobes, including two lateral lobes 104A and 104B, and a medial lobe 104C within a prostatic capsule "C". Upon stimulation, the bladder 102 constricts and urine (depicted by arrow "A") is released out of the urinary meatus 106 through the urethra 100.

Figure 2:
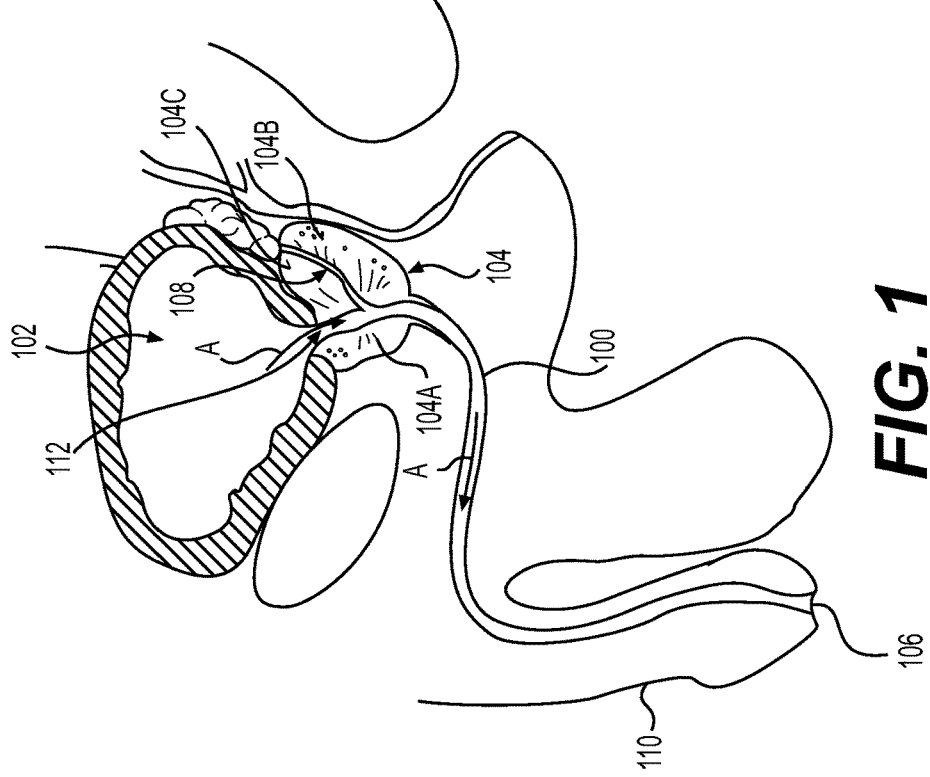
FIG. 2 illustrates a male pelvic region suffering from Benign Prostatic Hyperplasia (BPH)

FIG. 2 illustrates the male pelvic region suffering from Benign Prostate Hyperplasia (BPH). As shown, the pelvic region includes a urethra 200, a bladder 202, a prostate 204, a urinary meatus 206, an ejaculatory duct 208, a penis 210, and a bladder opening 212. In BPH, the passage of urine through the urethra 200 from the bladder 202 to the urinary meatus 206 at the tip of the penis 210 is obstructed by the enlarged prostate 204. For example, an excess tissue region 214 in the enlarged prostate 204, for example, excess tissue within one or more of the lateral or medial lobes 204A, 204B, and 204C (FIG. 3), may constrict (e.g., narrow, obstruct, and/or partially occlude) the urethra 200 proximate to the bladder opening 212, and may cause pain, difficulty in urination, and/or urinary infections. For example, due to constriction of the urethra 200, urine (depicted by arrow "B") is prevented from freely flowing through the urethra 200 to exit the penis 210 via the urinary meatus 206. In turn, it may result in urine buildup in the bladder 202. This accumulation of urine may increase infection and the occurrence of other urinary tract problems. In addition, the enlarged prostate 204 may constrict (e.g., narrow, obstruct, and/or partially occlude) the ejaculatory duct 208 causing erectile dysfunction or ejaculatory problems.

The enlarged prostate 204 may be severed using various methods, such as, enucleation as is known in the art. In enucleation, an energy emitting device, e.g., a laser, is used to cut (e.g., sever, ablate) tissue from remaining portions of the enlarged prostate 204. By way of example only, enucleation may be used to cut excess tissue region 214 from the enlarged prostate 204 in order to alleviate constriction of the urethra 200. One such energy-based surgical procedure includes Enucleation of the Prostate (EP). In this procedure, an energy source such as, for example, a holmium:YAG (Ho:YAG) laser, is used to remove obstructive prostate tissue. The Ho:YAG surgical laser is a solid-state, pulsed laser that emits light at a wavelength of approximately 2100 nm. This wavelength of light is particularly useful for tissue ablation as it is strongly absorbed by water. An advantage of Ho:YAG lasers is that they can be used for both tissue cutting and for coagulation. Energy-based surgical procedures, such as EP, are becoming increasingly preferred over previous methods (e.g., drug therapy) due to fewer complications requiring shorter hospital stays, shorter catheterization times, and shorter recovery times. While certain embodiments of this disclosure refer to the use of a Ho:YAG surgical laser, it is understood that additional or alternative energy sources may be used. Such sources may include RF energy emitting devices and non-HO:YAG surgical lasers having any appropriate wavelength.

As noted previously, EP procedures may require great skill and typically are performed by very experienced medical professionals. The procedure is "blind" in that incisions are made within the prostate 204 without a readily ascertainable sense of the "depth" or geometry of the prostate 204. As such, extreme care must be used so as to not inadvertently harm (e.g., cut, damage, etc) unintended portions of the prostate 204, including, for example, the ejaculatory ducts 208 and/or the prostatic capsule C which lines the prostate 204, as shown in FIG. 3. During an EP procedure, a medical professional may insert an energy emitting device, e.g., a laser, into the urethra 200 of a patient and direct energy toward one or more of the lateral lobes 204A and/or 204B and/or the medial lobe 204C so as to cut (e.g., separate) tissue. Following each cut of tissue via the energy emitting device, additional layers of the prostate 204 may become exposed and available for enucleation. However, as the medical professional continues to advance the energy emitting device so as to enuculeate deeper tissue portions within the prostate, he or she runs the risk of exposing and/or cutting the prostatic capsule C which may cause serious damage to nerves running therethrough, and consequently, increased pain and/or hemorrhage for a patient. Accordingly, it may be desirable to provide improved methods and systems for marking cutting planes within a prostate 204 to guide a medical professional during a procedure.

In an exemplary embodiment, as shown in FIG. 4A, a marking device 400 may include a body 410. Body 410 may comprise a clip or similar mechanism configured to fasten, grasp, squeeze, compress, or otherwise attach to target tissue. For example, body 410 may comprise a base 410a and legs 410b, 410c. As shown in FIG. 4A, in its natural unstressed state, the body 410 may be substantially triangular shaped such as a binder clip. For example, base 410a may extend along a first axis whereas legs 410b and 410c may respectively extend along second and third axes, each of the second and third axes being angled 45° in opposite directions away from the first axis. It is understood, however, that body 410 may include any shape suitable to fasten, grasp, squeeze, compress, or otherwise attach to target tissue.

A distal end of each leg 410b and 410c may be curved or otherwise autramatically manufactured. For example, a distal end of each leg 410b, 410c may comprise a rounded lip 420. Lips 420 may prevent or reduce damage to a patient during use of the marking device 400. Each rounded lip 420 of body 410 may be configured to receive a corresponding arm 430 of marking device 400. For example, as shown in FIG. 4A, a distal end 440 of each arm 430 may be received within the lip 420 of a respective leg 410b, 410c. Lips 420 and distal ends 440 may be complimentary shaped so as to mate or align with one another. For example, each distal end 440 may be shaped, arranged, or otherwise manufactured so as to be received within a recess, opening, or space within lip 420. In an unstressed state as shown in FIG. 4A, each arm 430 may extend substantially parallel to a respective one of legs 410b, 420c.

The body 410 may be comprised of a flexible material. For example, body 410 may be comprised of a plastic or metal material configured to bend upon actuation by the arms 430 as will be described in greater detail below. Examples of suitable materials may include, for example, metal, stainless steel, nichol-titanium alloy (e.g., NITINOL®), and/or plastic.

The body 410 may be coupled to an elongate member or suture 450 (e.g., string, wire, etc.). For example, as shown in FIG. 4A, suture 450 may be coupled to base 410a. It is understood, however, that suture 450 may be coupled to any portion of body 410 (e.g., base 410a and/or legs 410b, 410c) and/or arms 430. Suture 450 may be coupled to body 410 and/or arms 430 through any appropriate means such as, for example, tying, winding, gluing, heat-staking, and the like. Suture 450 may extend proximally of the body 410 to a location external of a patient for manipulation by a medical professional, as described in greater detail below. A proximal end of suture 450 may be coupled to a handle member 460. For example, as shown in FIG. 4A, handle member 460 may comprise a ring or weight configured to facilitate manipulation by a medical professional. Handle member 460 may have any suitable shape including, for example, a ring, t-bar, sphere, and the like.

Marking device 400 may be configured to transition between a first unstressed or closed configuration as shown in FIG. 4A, and a second stressed or open configuration as shown in FIG. 4B. For example, upon application of a force F on proximal ends of arms 430, as shown in FIG. 4B, arms 430 may be pushed, urged, or otherwise moved towards each other. Accordingly, and by way of cooperation between distal ends 440 and lips 420, body 410 may transition to its open configuration in which each distal end 440 moves away from one another. Due to each distal end 440 cooperating with, or otherwise being received by a respective lip 420, movement of the distal ends 440 away from one another causes a corresponding movement of legs 410b and 410c rotating away from one another in the directions shown in FIG. 4B. Accordingly, in the open configuration, the body defines a receiving space as shown in FIG. 4B, between legs 410b and 410c. Upon removal of the force F, marking device 400 may return to the first unstressed or closed configuration (FIG. 4A) due to its inherent material properties and configuration.

Figure 9:
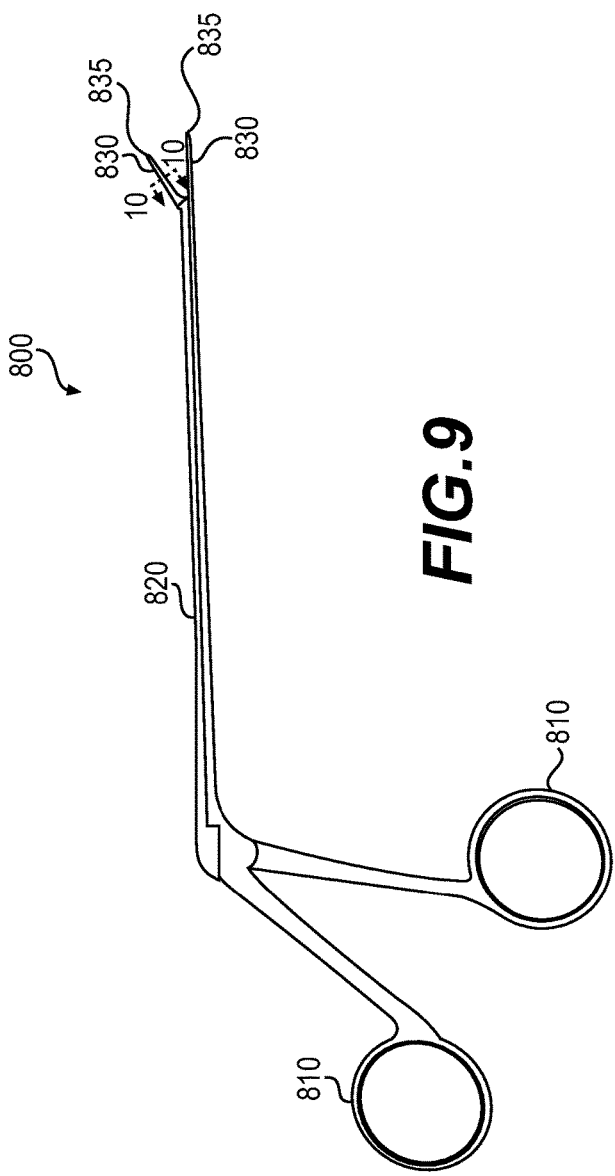
FIG. 9 illustrates an exemplary actuation device.
Figure 11:
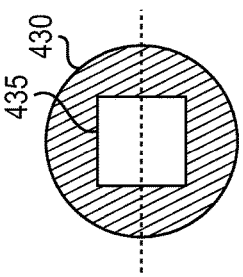
FIG. 11 illustrates an exemplary proximal end of an arm of the marking device shown in FIGS. 4A and 4B.
Figure 10:
FIG. 10 illustrates an exemplary distal end of the actuation device of FIG. 9.
Figure 12:
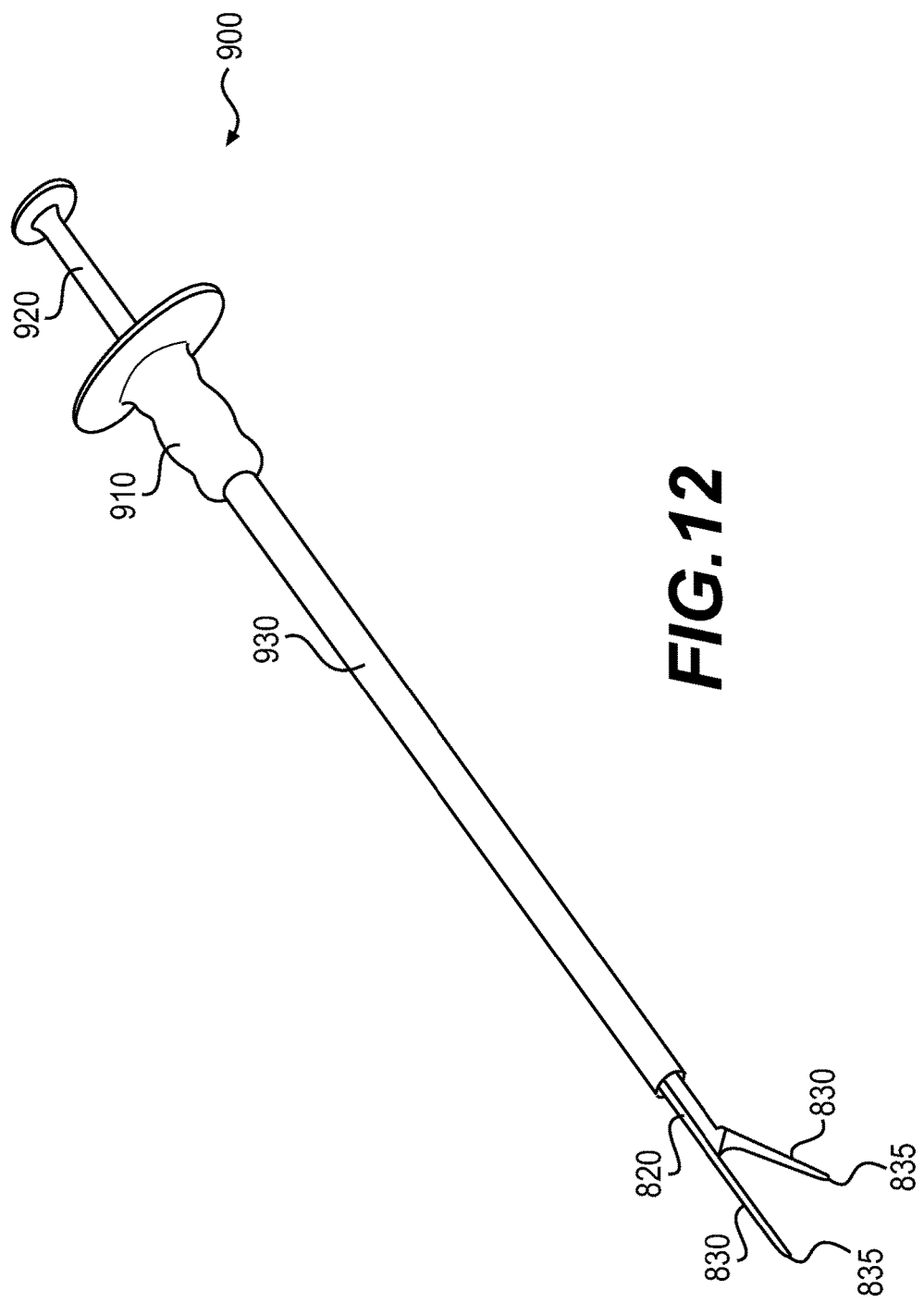
FIG. 12. illustrates another exemplary actuation device.
Figure 13:
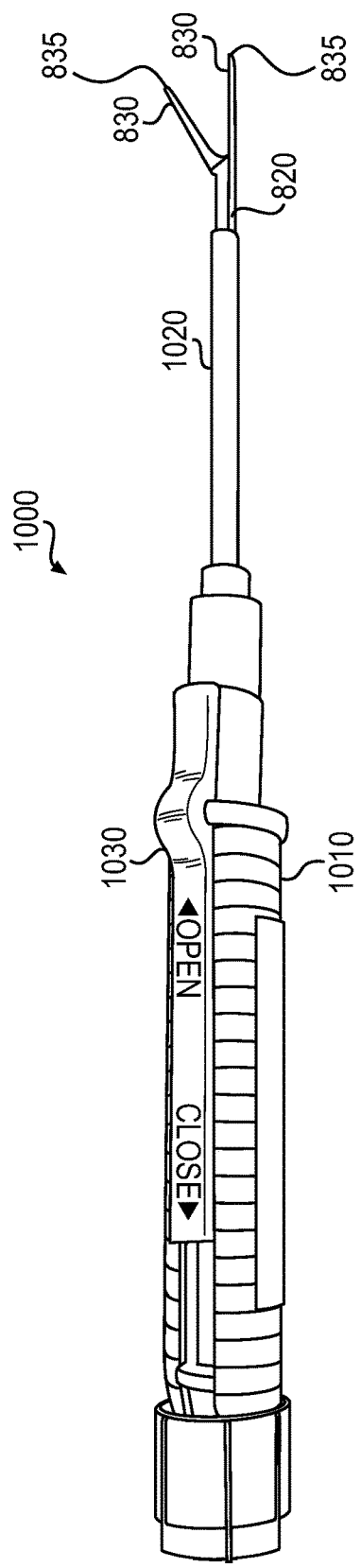
FIG. 13 illustrates yet another exemplary actuation device.

In one embodiment, force F may be applied to the proximal ends of arms 430 through a variety of actuation devices as shown in FIGS. 9, 12, and 13. For example, a forceps device 800, as shown in FIG. 9, may be used to cause marking device 400 to transition between the first unstressed or closed configuration as shown in FIG. 4A, and the second stressed or open configuration as shown in FIG. 4B. Forceps device 800 may be actuated in a manner similar to conventional scissors and may include a pair of finger and/or thumb rings 810 on a proximal end of a longitudinally extending body 820. Manipulation of the finger and/or thumb rings 810 causes a corresponding movement of first and second jaws 830 located on a distal end of the longitudinally extending body 820. For example, movement of rings 810 away from each other may cause first and second jaws 830 to open (e.g., spread apart from one another), and vice versa. A distal end of each jaw 830 and a proximal end of each arm 430 may be complimentary shaped. For example, a distal end of each jaw 830 may be a square shaped post 835 configured to be received within a correspondingly shaped recess 435 within the proximal end of arms 430, or vice versa. While a square shaped post 835 and recess 435 have been depicted and described, it is understood that such shaped are merely exemplary and that a variety of different complimentary shaped members may be used without departing from the scope of the disclosure.

Alternatively, forceps device 900 as shown in FIG. 12, may be used to cause marking device 400 to transition between the first unstressed or closed configuration as shown in FIG. 4A, and the second stressed or open configuration as shown in FIG. 4B. Forceps device 900 may be similar to forceps 800 except for the manner of actuation to cause jaws 830 to open and close. For example, instead of a pair of finger and/or thumb rings 810, forceps device 900 may include a handle 910 and push rod or plunger 920 configured to distally urge and/or retract longitudinally extending body 820, and consequently jaws 830, out of or into a sheath (e.g., rod, cylinder, and/or hypotube) 930. In such an embodiment, jaws 830 may be biased outwardly and plunger 920 may be coupled (e.g., attached or otherwise joined) to longitudinally extending body 820 such that a distally directed force on plunger 920 causes jaws 830 to extend distally of sheath 930. Once distal of sheath 930, jaws 830 may open due to their biased nature.

Alternatively, forceps device 1000 as shown in FIG. 13, may be used to cause marking device 400 to transition between the first unstressed or closed configuration as shown in FIG. 4A, and the second stressed or open configuration as shown in FIG. 4B. Forceps device 1000 may be similar to forceps 800 except for the manner of actuation to cause jaws 830 to open and close. For example, instead of a pair of finger and/or thumb rings 810, forceps device 1000 may include a handle 1010 and slider 1030 configured to distally urge and/or retract longitudinally extending body 820, and consequently jaws 830, out of or into a sheath (e.g., rod, cylinder, and/or hypotube) 1020 to open and close jaws 830. In such an embodiment, jaws 830 may be biased outwardly and slider 1030 may be coupled (e.g., attached or otherwise joined) to longitudinally extending body 820 such that a distally directed force on slider 1030 causes jaws 830 to extend distally of sheath 1020. Once distal of sheath 1020, jaws 830 may open due to their biased nature.

Delivery of the marking device 400 will be described in further detail with reference to FIGS. 5 and 6. For example, marking device 400 may be delivered to target tissue such as, for example, one or more lobes 204A-204C of prostate 204. Marking device 400 may be delivered to the one or more lobes 204A-204C by way of an insertion device (not shown) inserted through the urethra 200 of a patient. The insertion device may comprise a cystoscope, nephroscope, laserscope, or a rectoscope that may be inserted into the urethra 200 of a patient. The insertion device, as is known in the art, may be an endoscopic instrument that may be passed through the urethra 200 for visualization and/or manipulation of tissue. In some embodiments, the insertion device may have a substantially circular cross-sectional shape. Other suitable cross-sectional shapes such as elliptical, oval, polygonal, or irregular may also be contemplated.

The insertion device may include a vision system configured to aid a medical professional with accurate placement of one or more tools (e.g., marking device 400) within the body of the patient. The vision system may include lenses to focus an image, one or more optical fibers for transmitting light and/or images from a distal end of the insertion device to a viewing piece at a proximal end of the insertion device or a display device operably coupled with the one or more optical fibers, a vision chip (e.g., CCD, CMOS, etc.), a camera, and/or an illumination device to illuminate an interior of the body of a patient.

The insertion device may include a lumen (not shown) configured to receive the marking device 400 therein. Upon delivery of the insertion device through the urethra 200 to a position proximate target tissue, a medical professional may push, urge, or otherwise cause marking device 400 to extend distally of a distal end of insertion device. For example, in some embodiments, insertion device may include a stylet, tube, rod or the like 520 configured to extend within the lumen of the insertion device. The stylet 520 may provide sufficient columnar strength such that a medical professional may manipulate a proximal end of the stylet 520 so as to cause a distal end of the stylet 520 to push, urge, or otherwise cause marking device 400 to extend distally of the distal end of the insertion device.

Figure 5:
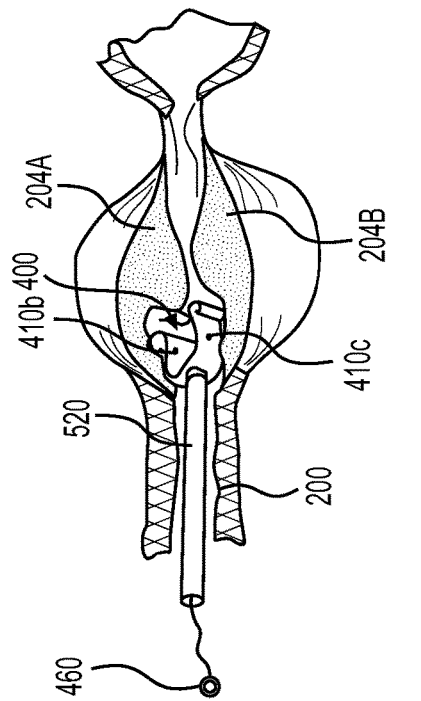
FIG. 5 illustrates the delivery of an exemplary marking device in vivo according to a first example.

As shown in FIG. 5, once positioned proximate target tissue, marking device 400, in which arms 430 have been removed for clarity, may be caused to transition to its stressed or open configuration (FIG. 4B). For example, an actuation device, e.g. any of forceps devices 800-1000, may be deployed through a lumen of the insertion device and positioned proximate the marking device 400. The medical professional may then urge the posts 835 of jaws 830 into the correspondingly shaped recesses 435 within the proximal ends of arms 430. Once coupled, the medical professional may cause the jaw 830 to apply force F on arms 430. Next, marking device 400 may be fastened or otherwise attached to target tissue as shown in FIG. 6. For example, marking device 400 may be positioned such that legs 410b and 410c receive target tissue, e.g., one or more lobes 204A-204C of the prostate, therebetween. Once positioned about target tissue, the force F (FIG. 4B) may be removed so as to allow marking device to transition to its unstressed or closed configuration (FIG. 4A), thereby fastening, grasping, squeezing, and/or compressing target tissue within marking device 400. That is, posts 835 may be removed from recesses 435 and the actuation device (e.g., any of forceps devices 800-1000) may be removed from the body of the patient. Once attached to target tissue, the stylet 520 may be removed while suture 450, coupled to the body 410, may extend through the urethra 200.

Figure 7:
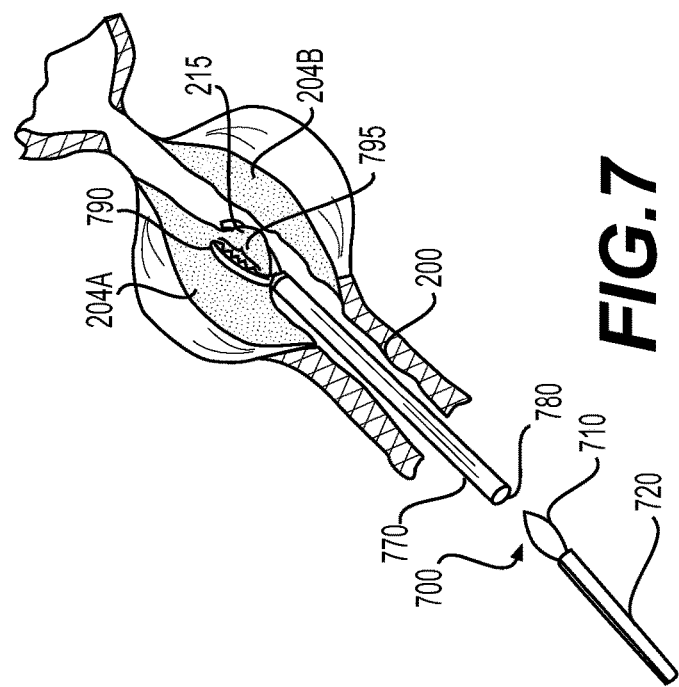
FIG. 7 illustrates the delivery of an exemplary marking device in vivo according to a second example.

In a second embodiment, as shown in FIG. 7, a marking device 700 may comprise an adjustable ligation member 710 (e.g., lasso, snare loop, etc.). Ligation member 710 may be configured to transition between a first collapsed configuration within a lumen of a sheath 720, and a second expanded configuration in which the ligation member 710 may be caused to extend outwards from a distal opening of the sheath 720. That is, in the collapsed configuration, the ligation member 710 may be compressed within the lumen of the sheath 720. Upon proper positioning within a patient's body such that a distal end of the sheath 720 is disposed adjacent target tissue, a medical professional may extend the ligation member 710 distally of (e.g., outward and away from) the sheath 720. Upon such action, the ligation member 710 may be relieved of the compression forces provided by the sheath 720. As such, the ligation member 710 may be free to transition into the expanded configuration. During use, the ligation member 710 may be caused to encircle the target tissue when in the expanded configuration. Thereafter, the ligation member 710 may be tightened about target tissue by retracting the ligation member 710 into the sheath 720 or the like such that the ligation member 710 may transition from the expanded configuration towards the collapsed configuration. Once tightened about target tissue, a lock (not shown) may be deployed to maintain the ligation member 710 tightly about target tissue. In some embodiments, the lock may be slidingly advanced along the marking device 700 but may be prevented from retracting along the marking device. For example, the lock may comprise a structure similar to the ratchet mechanism of a conventional zip tie.

A push/pull wire (not shown) may be operable to extend and retract the ligation member 710 such that the ligation member 710 may transition between the expanded and the collapsed configurations as is known in the art. For example, when a medical professional applies an axial force in a distal direction, the push/pull wire may extend (e.g., push) the ligation member 710 outwards from the sheath 720, thus moving the ligation member 710 into the expanded configuration. Similarly, when a medical professional applies an axial force in a proximal direction, the push/pull wire may retract (e.g., pull) the ligation member 710 into the sheath 720, thus moving the ligation member 710 into the collapsed configuration. In some embodiments, the push/pull wire and the ligation member 710 may be made of a continuous, e.g., monolithically formed unitary structure. However, in other embodiments, the push/pull wire and the ligation member 710 may be discrete and coupled to each other using any suitable technique known in art. Exemplary techniques may include welding, soldering, and/or heat bonding. While described as a wire, the push/pull wire may be comprised of a wire, or any other suitable elongate structure (e.g., elongate actuation member).

The ligation member 710 may be a wire in the form of a loop configured for surrounding, grasping, and/or severing target tissue. In some embodiments, the ligation member 710 can be a monofilament wire or a multifilament wire. The multifilament wire may be bonded, twisted together, crimped, and/or braided. In the illustrated embodiment, the ligation member 710 may form a substantially ovular loop shape. However, in some embodiments, the ligation member 710 may be configured to have any suitable loop shape such as, but not limited to, circular, hexagonal, rectangle, square, irregular, polygonal, semicircular, octagonal, or the like. Further, the ligation member 710 can be formed using any suitable biocompatible material such as, but not limited to metals, polymers, alloys, or the like. Exemplary materials may include steel, tungsten, NITINOL®, or titanium, and so forth.

In some embodiments, the ligation member 710 may be configured for electro-cauterization procedures. In such embodiments, the ligation member 710 and the push/pull wire may be formed from suitable conducting material, e.g., stainless steel or NITINOL®. The ligation member 710 may be configured to transmit electric current within specific ranges and be able to withstand repeated heating cycles during electro-cauterization procedure.

In some embodiments, the ligation member 710 comprises an elongate lasso structure having a first end and a second end and configured to transition between a first small diameter configuration and a second larger diameter configuration. A length of the ligation member 710 may be adjustable by positioning the first end relative to the second end, as is known in the art. During use, the ligation member 710 can be bent or stretched to a low profile, and be housed within a lumen of the sheath 720 in the first small diameter configuration. When the distal end of the sheath 720 is positioned at a desired location, the ligation member 710 can be deployed out of the lumen of the sheath 720. The length (and therefore, the size) of the ligation member 710 can be adjusted by positioning the first end relative to the second end, or vice versa. For example, increasing the length (and therefore, the size) of the ligation member 710 causes the ligation member to transition to the second larger diameter configuration as is known in the art.

Figure 8:
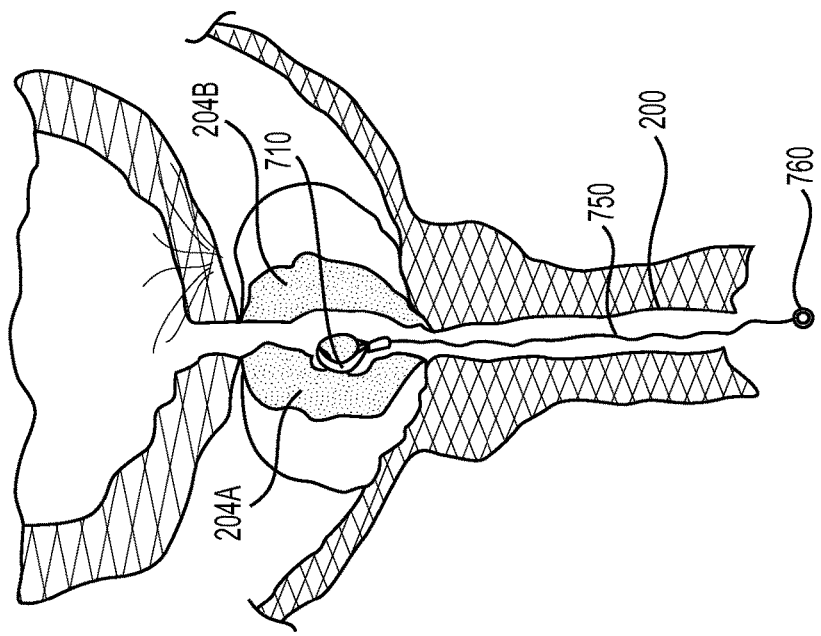
FIG. 8 illustrates the exemplary marking device after delivery in vivo according the second example.

Additionally, or alternatively, as shown in FIG. 8, marking device 700 may further include an elongate member or suture 750 (e.g., string, wire, etc.). For example, as shown in FIG. 8, suture 750 may be coupled to ligation member 710. Suture 750 may be coupled to ligation member 710 through any appropriate means such as, for example, tying, winding, gluing, heat-staking, and the like. Suture 750 may extend proximally of the ligation member 710 to a location external of a patient for manipulation by a medical professional, as described in greater detail below. A proximal end of suture 750 may be coupled to a handle member 760. For example, as shown in FIG. 8, handle member 760 may comprise a ring or weight configured to facilitate manipulation by a medical professional. Handle member 760 may have any suitable shape including, for example, a ring, t-bar, sphere, and the like.

Delivery of the marking device 700 will be described in further detail with reference to FIGS. 7 and 8. For example, marking device 700 may be delivered to target tissue such as, for example, one or more lobes 204A-204C of a prostate 204. Marking device 700 may be delivered to the one or more lobes 204A-204C by way of an insertion device (not shown) inserted through the urethra 200 of a patient. The insertion device may comprise a cystoscope, nephroscope, laserscope, or a rectoscope that may be inserted into the urethra 200 of a patient. The insertion device, as is known in the art, may be an endoscopic instrument that may be passed through the urethra 200 for visualization and/or manipulation of tissue. In some embodiments, the insertion device may have a substantially circular cross-sectional shape. Other suitable cross-sectional shapes such as elliptical, oval, polygonal, or irregular may also be contemplated.

The insertion device may include a vision system configured to aid a medical professional with accurate placement of one or more tools (e.g., marking device 700) within the body of the patient. The vision system may include lenses to focus an image, one or more optical fibers for transmitting light and/or images from a distal end of the insertion device to a viewing piece at a proximal end of the insertion device or a display device operably coupled with the one or more optical fibers, a vision chip (e.g., CCD, CMOS, etc.), a camera, and/or an illumination device to illuminate an interior of the body of a patient.

The insertion device may include one or more lumens (not shown) configured to receive and/or pass a manipulation tool 770 therethrough. Manipulation tool 770, as shown in FIG. 7, may include a lumen 780 through which ligation member 710 and sheath 720 may be passed as will be described in greater detail below. A working element or forceps 790 may be disposed on or about a distal end of manipulation tool 770. The forceps 790, as is known in the art, may include a textured gripping surface 795 configured to securely grip target tissue when actuated by a medical professional. For example, upon delivery of the insertion device through the urethra 200 of a patient to a position proximate target tissue, a medical professional, as is known in the art, may direct the manipulation tool 770 including forceps 790 through the insertion device such that the forceps 790 are located adjacent target tissue. Once positioned, a medical professional may actuate the forceps 790, as is known in the art, to clamp, squeeze, or otherwise grasp target tissue, such as one or more lobes 204A-204C of the prostate, therein. Grasping of the target tissue with the forceps, as shown in FIG. 7, creates a protruding tissue portion 215.

Once protruding tissue portion 215 is formed, a medical professional may push, urge, or otherwise cause marking device 700 to extend distally of a distal end of insertion device. For example, a medical professional may insert sheath 720 and ligation member 710 through lumen 780 of manipulation tool 770. Then, the medical professional may urge the sheath 720 to extend distally through the lumen 780 until a distal end of the sheath 720 and/or the ligation member 710 extend distally of the manipulation tool. Next, the medical professional may cause the ligation member 710 to transition from its first configuration to its second configuration. For example, a medical professional may apply an axial force in a distal direction on the push/pull wire to thereby extend (e.g., push) the ligation member 710 outwards from the sheath 720, thus moving the ligation member 710 into the expanded configuration. Alternatively, a medical professional may increase the length and therefore, the size) of the ligation member 710 such that the ligation member transitions to the second larger diameter configuration.

As shown in FIG. 8, once positioned proximate target tissue, marking device 700 may be fastened or otherwise attached about protruding tissue portion 215. That is, ligation member 710 may be caused to encircle or surround protruding tissue portion 215 and ligation member 710 may be tightened thereabout. In other words, once placed about the protruding tissue portion 215, a medical professional may apply an axial force in a proximal direction on the push/pull wire to thereby retract (e.g., pull) the ligation member 710 towards the sheath 720, thus moving the ligation member 710 into the collapsed configuration. Alternatively, a medical professional may decrease the length (and therefore, the size) of the ligation member 710 such that the ligation member transitions to the first small diameter configuration. Once attached to target tissue, the sheath 720 and/or the manipulation tool 770 may be removed while suture 750, coupled to the ligation member 710, may extend through the urethra 200. Once tightened about target tissue, a lock (not shown) may be deployed to maintain the ligation member 710 tightly about target tissue as described above.

Figure 6:
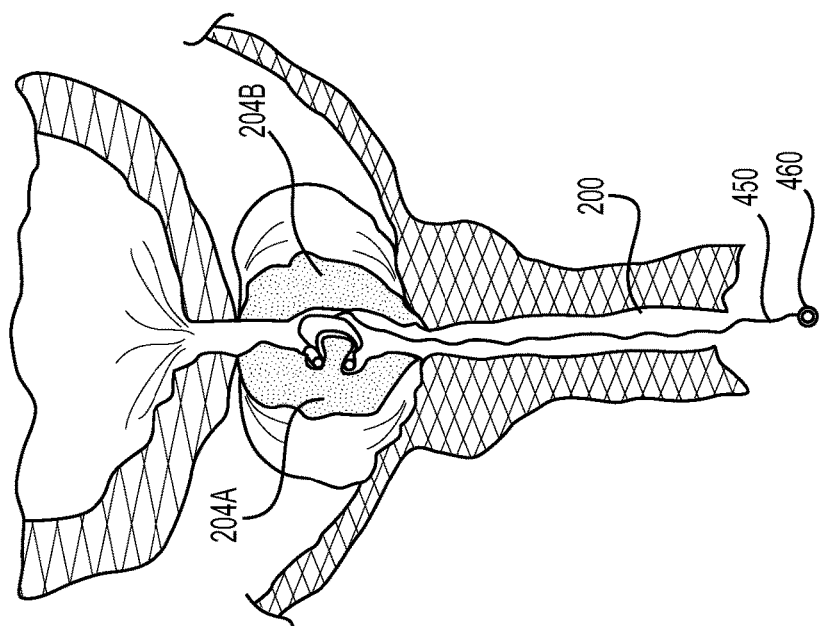
FIG. 6 illustrates the exemplary marking device after delivery in vivo according the first example.

As shown in FIGS. 6 and 8, once marking device 400 and/or 700 is positioned about target tissue (e.g., one or more of lobes 204A-204C), the selected target tissue is readily distinguishable from remaining portions of the prostate, including, for example, a capsule C (FIG. 3). Following placement of marking device 400 and/or 700 about or on target tissue, the insertion device may be removed. Next, a laserscope (not shown) may be inserted into the urethra 200 of the patient. Any readily available and appropriately sized laserscope may be used. The laserscope may include a lumen (e.g., working channel) through which an energy emitting device (e.g., a holmium:YAG (Ho:YAG) laser) may be passed. For example, in some embodiments, the energy emitting device and/or a lumen of the laserscope may be coated with or comprised of a lubricious material to facilitate smooth insertion of the energy emitting device through the lumen of the laserscope. Additionally, the laserscope may include a vision system configured to aid a medical professional with accurate placement of the energy emitting device within the body of the patient. The vision system may include lenses to focus an image, one or more optical fibers for transmitting light and/or images from a distal end of the laserscope to a viewing piece at a proximal end of the laserscope or a display device operably coupled with the one or more optical fibers, a vision chip (e.g., CCD, CMOS, etc.), a camera, and/or an illumination device to illuminate an interior of the body of a patient.

Once the laserscope is positioned within the urethra 200 of the patient, the energy emitting device may be inserted through the lumen of the laserscope such that a distal end of the energy emitting device is adjacent the target tissue portion. As noted above, the laserscope may include a vision system to guide a medical professional during placement of the laserscope adjacent the target tissue portion. After positioning, the medical professional may activate the energy emitting device and direct laser energy emitted therefrom toward the target tissue. By virtue of marking device 400 and/or 700, the target tissue may be readily distinguishable from remaining portions of the prostate, including the capsule C on the laserscope vision system. Accordingly, a medical professional may quickly and confidently direct the energy emitted from energy emitting device without harming the capsule C. Accordingly, the disclosed devices and methods enable increasingly efficient and safer enucleation of a patient's prostate.

Enucleating, cutting, and/or severing of target tissue may form a tissue ball. Once formed, the tissue ball and marking device 400, 700 may be moved (e.g., pushed) into the bladder 202 (FIG. 2) for removal via an appropriate tool. For example, in some embodiments, a rectoscope or other scope device may be inserted into the patient's urethra 200 for introduction of a tissue extraction device. Such extraction devices may include, for example, a high-pulse energy emitter to destroy the tissue ball, or a morcellating tool to cut the tissue ball into small pieces.

In some embodiments, for example, a morcellating tool (not shown) may be advanced towards one or more enucleated tissue balls in the bladder 202. A morcellator is a surgical device having a small opening at its distal end, one or more cutting blades, and suction capability. The blades may cut (e.g., mince, puree) the large pieces of tissue, e.g., tissue balls, that were moved into the bladder 202 into smaller pieces. These smaller pieces may then be removed out of the body through the opening via, suction and/or other means.

Generally, tissue balls that are pushed into the bladder 202 float freely within the bladder 202 and have a tendency to avoid capture by bouncing off the bladder wall and/or floating away from the morcellator device, which makes it difficult to contact the tissue balls for morcellation. In some embodiments, the suture 450, 750 and/or the handle member 460, 760 of one or more marking devices 400, 700 may be coupled to the morcellator device. For example, the morcellator device may include a loop, hook, extension, or other structure configured to be coupled to one or more of suture 450, 750 and/or handle member 460, 760. One or more of suture 450, 750 and/or handle member 460, 760 may be coupled to the morcellator device via tying or any other appropriate means by a medical professional. Once coupled, the marking device 400, 700, being securely coupled to the tissue ball and the morcellating device, may prevent the enucleated tissue balls from bouncing/floating away from the morcellator device during use.

While embodiments described herein include the introduction of multiple scope/insertion devices, e.g., a rectoscope, cystescope, nephroscope, and/or a laserscope, it is understood that in some embodiments, a single fully equipped scope device may be used to introduce marking device 400 and/or 700, energy emitting device, and a tissue extractor (not shown) without departing from the scope of the disclosure.

Using the exemplary devices and methods described herein, a medical professional may readily and accurately remove enlarged prostatic tissue from a patient's body for treatment or diagnostic purposes. It is understood, however, that while embodiments of the present disclosure have been described in reference to treating BPH, the teachings of the present disclosure may be used to treat other tissues and/or disorders. Further, the devices herein may be single-use which can be discarded after one use or may be used again after sterilization.

Other embodiments of the present disclosure will be apparent to those skilled in the art after consideration of the specification and practice of the embodiments disclosed herein. It is intended that the specification and examples be considered as exemplary only, with a true scope and spirit of the disclosure being indicated by the following claims.

What is claimed is:

1. A marking device for a medical procedure, comprising:
   a body including two legs, wherein the body is configured to transition between a closed and unstressed configuration and an open configuration;
   two arms, wherein a distal end of each arm is coupled to a distal end of the body; and
   a suture coupled to the body,
   wherein application of a force on a proximal end of each arm is configured to cause the body to transition from the closed and unstressed configuration to the open configuration;
   wherein in the open configuration, distal ends of each leg are spaced apart from one another by a first distance, and wherein in the closed and unstressed configuration, the distal ends of each leg are spaced apart from one another by a second non-zero distance, wherein the first distance is greater than the second distance;
   wherein the distal end of each led includes a rounded lip; and
   wherein the distal end of each arm is received within a recess in the rounded lip of a respective one of the legs.

2. The marking device of claim 1, wherein the body comprises a clip.

3. The marking device of claim 1, wherein, in the open configuration, the body defines a receiving space.

4. The marking device of claim 3, wherein the receiving space is configured to retain tissue therein.

5. The marking device of claim 1, wherein a shape of the distal end of each arm is complementary to a shape of each lip.

6. The marking device of claim 1, wherein the body comprises at least one of stainless steel, plastic, and Nitinol.

7. The marking device of claim 1, wherein the suture includes a length sufficient to extend externally of a patient when the marking device is internal of a patient.

8. The marking device of claim 1, wherein a handle member is coupled to a proximal end of the suture.

9. A marking device for a medical procedure, comprising:
   a body including a base and two legs, wherein the legs extend at an angle relative to the base from curved connection portions, wherein the body is configured to transition between a closed configuration and an open configuration, and wherein a distal end of each leg includes a rounded lip;
   two arms, wherein a distal end of each arm is received with a recess in the rounded lip in the distal end of one of the legs; and a suture coupled to a middle portion of the base; and
   wherein application of a force on a proximal end of each arm is configured to cause the body to transition between the closed configuration and the open configuration, and
   wherein in the closed configuration there is a non-zero gap between the distal ends of the legs, and wherein the closed configuration is an unstressed configuration.

10. The marking device of claim 9, wherein in the closed configuration, the legs extend from the base at a first acute angle to form a partially triangular shape with the gap forming a distal opening opposite to the base.

11. The marking device of claim 10, wherein in the open configuration, the legs extend from the base at a second acute angle larger than the first acute angle to form a partially trapezoidal shape, wherein the distal opening in the open configuration is larger than the distal opening in the closed configuration.

12. The marking device of claim 11, wherein the suture is coupled to the middle portion of the base opposite to a central portion of the distal opening.

13. The marking device of claim 9,
   wherein a shape of each distal end of each arm is complementary to a shape of each lip.

14. A marking device for a medical procedure, comprising:
   a body configured to transition between a first configuration and a second configuration, wherein the body includes a base and two legs extending distally from the base, wherein a distal end of each leg includes a rounded lip, wherein the first configuration is an unstressed configuration in which the two legs are spaced apart by a non-zero first distance, and wherein the second configuration is a stressed configuration in which the two legs are spaced apart by a second distance greater than the first distance;
   two arms, wherein a distal end of each arm is received with a recess in the rounded lip in one of the two legs; and
   a suture coupled to a middle portion of the base, wherein the middle portion of the base is equidistant from the connections of the two legs to the base, and wherein the middle portion of the base is substantially aligned with a center point of the first distance when the body is in the first configuration and with a center point of the second distance when the body is in the second configuration,
   wherein application of a force on a proximal end of each arm is configured to cause the body to transition between the first configuration and the second configuration.

15. The marking device of claim 14, further including a stylet, wherein the suture extends proximally of the body and through the stylet.

16. The marking device of claim 15, wherein the suture includes a length sufficient to extend externally of a patient when the marking device is internal of a patient.

* * * * *